(12) United States Patent
Zabaleta et al.

(10) Patent No.: US 12,138,443 B2
(45) Date of Patent: Nov. 12, 2024

(54) DEVICE AND SYSTEM FOR FUNCTIONAL ELECTRICAL STIMULATION

(71) Applicant: FESIA TECHNOLOGY, S.L., San Sebastián (ES)

(72) Inventors: Haritz Zabaleta, San Sebastián (ES); Eukene Imatz, San Sebastián (ES); Thierry Keller, San Sebastián (ES)

(73) Assignee: FESIA TECHNOLOGY, S.L., San Sebastian (ES)

( * ) Notice: Subject to any disclaimer, the term of this patent is extended or adjusted under 35 U.S.C. 154(b) by 638 days.

(21) Appl. No.: 17/291,766

(22) PCT Filed: Nov. 6, 2019

(86) PCT No.: PCT/EP2019/080371
§ 371 (c)(1),
(2) Date: May 6, 2021

(87) PCT Pub. No.: WO2020/099207
PCT Pub. Date: May 22, 2020

(65) Prior Publication Data
US 2021/0386993 A1  Dec. 16, 2021

(30) Foreign Application Priority Data
Nov. 12, 2018  (EP) .................... 18380012

(51) Int. Cl.
*A61N 1/04* (2006.01)
*A61N 1/36* (2006.01)
*A61N 1/32* (2006.01)

(52) U.S. Cl.
CPC ....... *A61N 1/0484* (2013.01); *A61N 1/36031* (2017.08); *A61N 1/0452* (2013.01); *A61N 1/0456* (2013.01); *A61N 1/36003* (2013.01)

(58) Field of Classification Search
CPC .............. A61N 1/0484; A61N 1/36031; A61N 1/0452; A61N 1/0456; A61N 1/36003;
(Continued)

(56) References Cited

U.S. PATENT DOCUMENTS 5,562,707 A * 10/1996 Prochazka ......... A61N 1/36003
607/2
5,643,332 A  7/1997 Stein
(Continued)

FOREIGN PATENT DOCUMENTS

| EP | 2519312 B1 | 5/2014 |
| WO | 2007057899 A2 | 5/2007 |
| WO | 2015188889 A1 | 12/2015 |

OTHER PUBLICATIONS

International Search Report issued Jan. 24, 2020 re: Application No. PCT/EP2019/080371, pp. 1-4, citing: US 2017/106189 A1, US 2018/250520 A1, WO 2007/057899 A2, US 2012/310303 A1.
(Continued)

*Primary Examiner* — Lynsey C Eiseman
*Assistant Examiner* — Christopher J Mutchler
(74) *Attorney, Agent, or Firm* — CANTOR COLBURN LLP (57) ABSTRACT

A device for functional electrical stimulation, including a garment mountable on a user's body part, an assembly having a socket and an electrode in turn having electrode pads and a stimulator with a controlling mechanism for activating/deactivating stimulating electrical signals to be provided to at least some of the electrode pads. The garment defines a hollow area configured to receive the socket, the socket configured to house the stimulator. In use of the device, a first portion of the electrode is in contact with an inner surface of the garment, the electrode pads are in a fixed position with respect to the garment, and a second portion of the electrode is in contact with a surface of the socket for
(Continued)

receiving the stimulating electrical signals delivered by the stimulator. A system may include the device and a sensor configured to be positioned on either user or in proximity thereto.

14 Claims, 10 Drawing Sheets

(58) Field of Classification Search
CPC .............. A61N 1/3603; A61N 1/36014; A61N 1/0476; A61N 1/321
See application file for complete search history.

(56) References Cited

U.S. PATENT DOCUMENTS

| | | | |
|---|---|---|---|
| 9,878,153 B2 | 1/2018 | Keller et al. | |
| 2002/0077688 A1* | 6/2002 | Kirkland | A61N 1/36034 607/142 |
| 2004/0254624 A1* | 12/2004 | Johnson | A61N 1/0492 607/48 |
| 2007/0027387 A1* | 2/2007 | Fendrock | A61N 1/0456 600/382 |
| 2007/0106343 A1* | 5/2007 | Monogue | A61B 5/296 607/48 |
| 2012/0172940 A1* | 7/2012 | Wahls | A61N 1/0476 607/3 |
| 2012/0310303 A1 | 12/2012 | Popovic et al. | |
| 2012/0330395 A1* | 12/2012 | Dar | A61N 1/0484 607/149 |
| 2013/0077263 A1* | 3/2013 | Oleson | A41D 1/005 361/747 |
| 2014/0257436 A1* | 9/2014 | Yonce | A61N 1/36017 607/148 |
| 2016/0008597 A1* | 1/2016 | Chen | A61N 1/3603 607/60 |
| 2016/0045721 A1* | 2/2016 | Bachinski | A61N 1/048 607/149 |
| 2017/0106189 A1 | 4/2017 | Keller et al. | |
| 2018/0250520 A1 | 9/2018 | Hyde et al. | |

OTHER PUBLICATIONS

Written Opinion issued Jan. 24, 2020 re: Application No. PCT/EP2019/080371, pp. 1-6, citing: US 2017/106189 A1, US 2018/250520 A1 and WO 2007/057899 A2.

* cited by examiner

DEVICE AND SYSTEM FOR FUNCTIONAL ELECTRICAL STIMULATION

TECHNICAL FIELD

The present disclosure relates to the field of functional electrical stimulation (FES) and, in particular, to apparatuses for external activation of paralyzed or impaired body parts by electrostimulation of peripheral nerves, such as for treating drop-foot disorders and/or hand function disorders.

STATE OF THE ART

Neurological injuries or disorders, such as stroke, spinal cord injury or cerebral palsy, among others, usually cause complete or partial paralysis of body parts. Although muscles may be connected to the central nervous system (CNS), they may be functionally paralyzed. Functional electrical stimulation (FES) is a technique that uses low energy electrical pulses to artificially generate muscle contractions in order to produce body segment movements and motor functions such as grasping or walking, in individuals who have been paralyzed as a consequence of such injuries.

There exist apparatuses for external activation of paralyzed body parts by stimulation of peripheral nerves based on FES. For example, EP2519312B1 discloses a sleeve designed to be worn by a user. The sleeve comprises a stimulation layer having multi-pad electrodes, configured to be in contact with the user's skin, and an activation layer opposite the stimulation layer and overlapping it, composed of pressure sensors for activating/deactivating corresponding pads of the stimulation layer.

A common consequence of neurological disorders is called drop-foot. Drop-foot refers to the inability or difficulty of making a dorsiflexion movement or the ankle and is a result of an interruption or severance of the communication path between the brain, motor nerves and leg muscles. Use of FES devices has been reported to enable drop-foot patients to lift their foot periodically as part of a close to natural gait cycle. WO2015188889A1 discloses a functional electrical stimulation device and method for correction of drop-foot. The disclosed device comprises a garment designed to be placed on a leg of a user suffering from drop-foot. Integrated into the garment there is a plurality of electrode pads designed to be in contact with the user's skin. Attached to the garment there is a housing having stimulation means for selectively stimulating the electrode pads.

Another FES device is disclosed in U.S. Pat. No. 5,643, 332A. It is composed of a band, mountable on a limb, made of stretchable material. A cathode electrode and an anode electrode are attached to the band with conductive snap connectors. Once the optical placement of the electrodes is determined by a technician or clinician, holes are punched through the band and the electrodes are fitted through the corresponding holes. In order to correctly position the device on the user's leg, a metal plate is fixed to the band, in such a way that the metal plate can be bent to conform to the anterior position of the tibia. Once bent, the plate can be located reproducibly on the tibia.

However, a user may have difficulties in using this device, not only because it requires the presence of a technician or clinician for determining the optimal position of the two electrodes, but also because relying on a bent metal plate for determining the correct position of the device on the user's leg may lead to incorrect positioning thereof, since a bent metal plate may fit in different positions of the user's leg, only one being the optimal.

SUMMARY

The drawbacks of conventional functional electrical stimulation devices are solved by the present disclosure, which provides a functional electrical stimulation device which is very easy to use, even for a person having suffered a neurological injury.

The functional electrical stimulation device of the present disclosure is a rehabilitation device designed to provide motor functions to persons having difficulty moving a limb as a result of a central nervous system disease or injury. During the movement or activity of the user, the device electrically stimulates the motor nerves of the affected limb to achieve the corresponding function, so that the user improves his/her activity. Functional electrical stimulation can also enhance motor relearning, strengthen muscles, prevent or delay muscle atrophy, increase local blood flow and/or maintain/increase range of motion. In a particular embodiment, a device for functional electrical stimulation provides dorsal flexion and plantar flexion of the ankle to persons suffering from foot drop. During gait, the device electrically stimulates the motor nerves of the affected leg to achieve dorsal flexion and plantar flexion of the foot, so that the user improves his gait. In another particular embodiment, a device for functional electrical stimulation provides flexion and extension of the knee. In another particular embodiment, a device for functional electrical stimulation provides flexion and extension of the elbow to persons suffering from difficulties in moving the arm and forearm. During flexion and extension of the elbow, the device electrically stimulates the motor nerves of the biceps and triceps. In another particular embodiment, a device for functional electrical stimulation provides flexion and extension of the wrist and independent flexion and extension of the fingers. During flexion and extension of the wrist and fingers, the device electrically stimulates the corresponding muscle groups.

In a first aspect of the disclosure, a device for functional electrical stimulation is provided. The device comprises: a garment, such as a textile or fabric garment, mountable on a user's body part; an assembly comprising a socket and an electrode or electrode patch; and a stimulator. The electrode or electrode patch has a plurality of electrode pads. The electrode pads are implemented on or embedded in the electrode or electrode patch. The plurality of electrode pads comprises at least one active electrode pad and at least one return electrode pad. The stimulator comprises means for controlling the activation/deactivation of stimulating electrical signals to be provided to at least some of the plurality of electrode pads. In use of the device, a surface of the electrode or electrode patch lays along an inner surface of the garment, while the opposite surface of the electrode or electrode patch is in contact with the user's skin, preferably by means of a skin-electrode hydrogel interface. The garment defines a hollow area configured to receive the socket. The socket is configured to house the stimulator. In use of the device, a first portion of the electrode is in contact with an inner surface of the garment, the electrode pads of the electrode being in a fixed position with respect to the garment, and a second portion of the electrode is in contact with a surface of the socket for receiving the stimulating electrical signals delivered by the stimulator. That is to say, when the hollow area receives the socket, the electrode or electrode patch and the electrode pads comprised therein, are disposed in a fixed position with respect to the garment.

In embodiments of the disclosure, the garment has fastening means for securement of the garment to or around a user's body part.

In embodiments of the disclosure, the electrode comprises a substrate on which the electrode pads are implemented.

In embodiments of the disclosure, the electrode comprises a conductive layer disposed on the surface of the electrode pads intended to be in contact with the user's skin.

In some areas of the electrode or electrode patch, such as the area configured to be in contact with the socket, the electrode patch may have an adhesive film, such as glue, in order to guarantee proper adhesion to the socket and prevent relative movement between the electrode patch and the socket.

In embodiments of the disclosure, the assembly comprising the electrode and the socket is reusable.

In embodiments of the disclosure, the means comprised in the stimulator for controlling the activation/deactivation of stimulating electrical signals to be provided to at least some of said plurality of electrode pads, are electronic means for generating electronic patterns.

In embodiments of the disclosure, in use of the device, the stimulator is securely coupled to the socket, the socket and the stimulator having mechanical means for mechanically fixing the socket and the stimulator in a single position.

In embodiments of the disclosure, the socket is error-free, the socket having means for guaranteeing that the stimulator cannot be switched on when it is not housed in the socket.

In embodiments of the disclosure, the outer surface of the garment has screen-printed marks for aligning the device with respect to the user's body part on which it is placed.

In embodiments of the disclosure, the garment is error-free, the surface of the garment being configured to have the electrode disposed thereon, said surface having the shape of the electrode pads screen-printed.

In embodiments of the disclosure, the garment has a left-right indication in order to make more visible whether the electrode has been correctly positioned or not.

In embodiments of the disclosure, the garment is made of a plurality of portions each of which, in use of the device, form a ring around the user's arm; wherein the garment has an area which is common to the plurality of portions and each portion has a tongue or elongated part independent from the tongues or elongated parts of the other portions of said plurality of portions.

In a second aspect of the disclosure, a system for functional electrical stimulation is provided. The system comprises: the device already disclosed; and a sensor configured to be positioned on either said body part of the user or in the proximity thereto, the sensor being configured to, in use of the system, measure information during movement and emit sensor signals indicative thereof, to be received and processed by the stimulator comprised in the device. The stimulator controls the activation/deactivation of stimulating electrical signals to be provided to at least some of said plurality of electrode pads as a function of the sensor signals provided by the sensor.

In embodiments of the disclosure, the stimulator and the sensor are connected through a wireless connection.

In embodiments of the disclosure, the system further comprises control means for controlling the operation of the device, the control means being embedded in an electronic device having processing means, the control means comprising a computer program, software or application for controlling and configuring the execution of the device, the control means communicating with the stimulator comprised in the device through a wireless protocol. That is to say, in the control means, a computer program, software or application is run, for controlling and configuring the parameters and execution of the functional electrical stimulation. The control means may be embodied as an application, computer program or software running from or in a personal computer, tablet, smart phone or any other electronic device comprising processing means capable of executing the corresponding application or computer program or software.

The design of both the device and the system is modular. This means that each module or element of the device and/or system is designed separately and independently from the rest of the modules or elements, at the same time that they are compatible with each other. Therefore, the costs of maintenance, design, certification, etc., as well as the launch times of new products, are significantly reduced. As a consequence, it is easier to continue developing each module separately, always maintaining compatibility between them.

In addition, the stimulator and the socket are unique (universal) for any device or system intended to rehabilitate any part of the body. Different electrodes, even if intended to be used for different body segments, are delivered with a unique socket. So by choosing the correct electrode patch—delivered with a universal socket—and the stimulator purchased with a rehabilitation kit from another part of the body, the stimulator can be reused.

In addition, having a fully modular system simplifies the development of future products to stimulate other body parts or muscle groups. It would be enough to design the electrode or electrode patch so that areas of the electrode patch are placed at certain anatomical points (nerve innervation points/above the corresponding nerve), a garment that suits the shape of the place where the electrode patch should be positioned, and the required software application(s) and stimulating patterns, for easiness of configuration. The stimulator would not require further development, as the software it contains allows it to be configured in a very flexible way. The socket would not require further development either.

Additional advantages and features of the disclosure will become apparent from the detail description that follows and will be particularly pointed out in the appended claims.

BRIEF DESCRIPTION OF THE DRAWINGS

To complete the description and in order to provide fora better understanding of the disclosure, a set of drawings is provided. Said drawings form an integral part of the description and illustrate an embodiment of the disclosure, which should not be interpreted as restricting the scope of the disclosure, but just as an example of how the disclosure can be carried out. The drawings comprise the following figures:

In FIG. 5A a socket to which the stimulator may be attached, is also schematized.

In FIG. 6A, both elements are not coupled yet. In FIG. 6B, both elements have been coupled and the recess in the socket fits with the protrusion in the stimulator.

DETAILED DESCRIPTION OF THE DRAWINGS

Figure 1A:
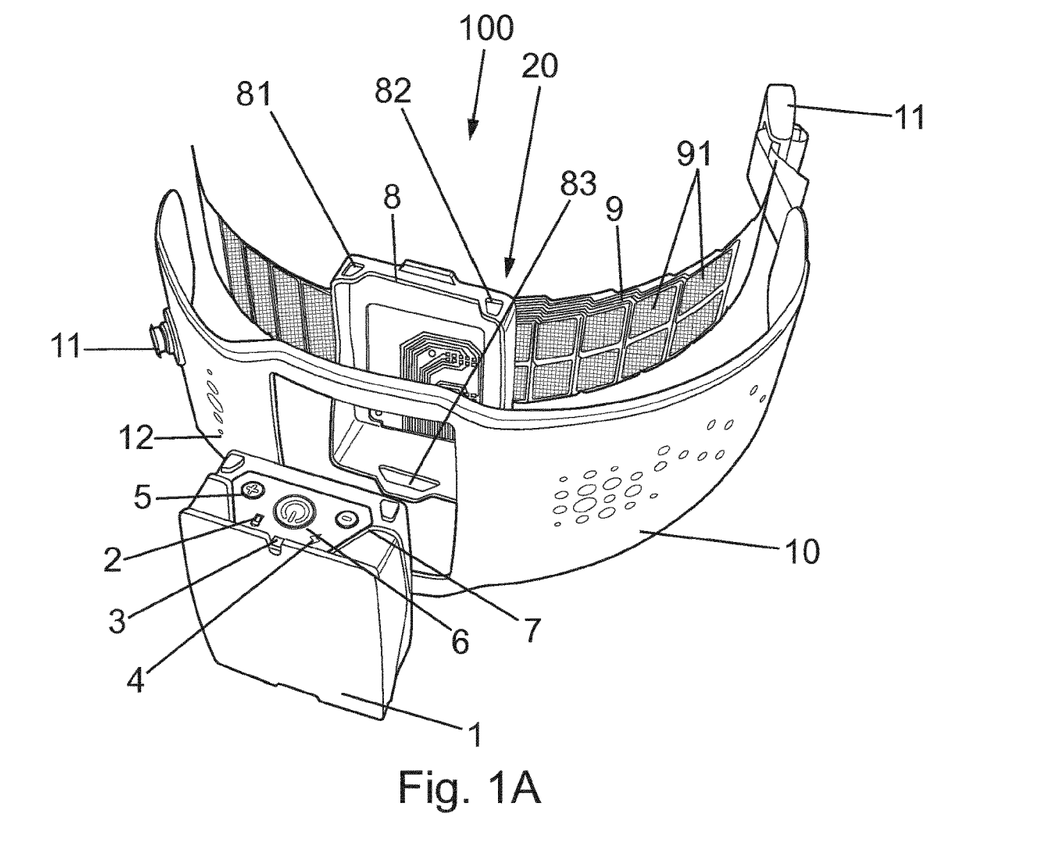
FIG. 1A shows an exploded view of a device for functional electrical stimulation according to a possible implementation of the disclosure.

FIG. 1A shows an exploded view of a device 100 for functional electrical stimulation according to a possible implementation of the disclosure. The device 100 of this embodiment has several modules or elements. The device 100 does not require wires.

A first element of device 100 is a garment 10, such as a textile or fabric garment. Because the device 100 does not need wires, the garment 10 can be manufactured with flexible materials or fabrics that adapt to the shape of the user's body or limb. This makes the process of positioning and/or wearing the device 100 very easy. In other words, the garment 10 is designed and manufactured in an ergonomic way. The ergonomic garment 10 also contributes to enhance the autonomy of the patient, who can even put it on with a single hand or at least without the need of external help. The garment 10 is preferably made of breathable materials. In use of the device 100, as disclosed next, an assembly 20 comprising an electrode 9 and a socket 8 is attached to the garment 10, that is designed in a manner which allows positioning of the assembled device 100 in just one possible way; thereby facilitating the use of the device 100. In embodiments of the disclosure, the garment 10 has fastening means, for example at its ends, for securement of the garment around a user's body segment (forearm, upper arm, thigh, shank, among others). For example, when the device 100 is for stimulating a foot or hand function, the garment 10 may secure the device 100 around the user's shank or forearm, respectively, in the form of a ring.

A second element of device 100 is an assembly 20 having a socket 8 and an electrode or electrode patch 9. The electrode or electrode patch 9 comprises, among other things, a plurality of electrode pads 91. Therefore, the electrode or electrode patch 9 is a multi-pad electrode. The electrode 9 is designed to be attached to or in contact with the garment 10, thus being carried by the garment 10 in a stationary or fixed condition, in such a way that the electrode pads 91 comprised in the electrode 9 are disposed on fixed positions of the garment 10. The socket 8 provides physical interface to receive a stimulator and to keep the electrode 9 mechanically and electrically attached to the stimulator. When the garment 10 is worn by a user, the electrode pads 91 are in contact with the user's skin preferably by means of a hydrogel layer, which acts as an interface between the skin and the electrode pads 91. Depending on the part of the body to be stimulated, the electrode or electrode patch 9 may be elongated.

The electrode 9 is made of different elements disposed in a layered configuration. In a lower layer, the electrode 9 has a substrate that may be made of a plastic material, for example, polyethylene terephthalate (PET) or polyamide. The substrate may also be a silicone-based substrate. The substrate may also be made of a non-woven fabric. Electrode pads 91 are defined on the substrate. Electrode pads 91 are made of a conductive material. For example, electrode pads 91 may be made of metal, such as copper, gold or silver. In other embodiments they may be made of graphite. Electrode pads 91 may be printed by means of biocompatible ink, such as silver ink, graphite ink or a combination of inks of different conductive materials.

The electrode 9 may comprise a conductive gel, such as hydrogel, disposed covering the electrode pads 91, intended to be in contact with the user's skin. More particularly, the conductive gel may be disposed on the layer defining the electrode pads 91, such as layer of ink, therefore between the electrode pads and the user's skin. The conductive gel has the function of being an interface between the electrode pads 91 and the skin. The layer of conductive gel covering the electrode pads may be covered by a protective layer. On the surface of the substrate of the electrode designed to be in contact with the socket 8, a layer of background adhesive may be disposed. A film, such as a film of release liner, for example made of a plastic material, such as PET, covers the surface impregnated with adhesive. The film is removed prior to locating the corresponding part of the substrate of the electrode 9 on the respective surface of the socket 8. The electrode 9 may also have an insulating layer, such as a dielectric layer, for guaranteeing that only the electrode pads 91 can make electrical contact with the user's skin.

The optimal placement of the electrode pads 91 on the user's body part, and therefore the garment 10 which carries the electrode having the electrode pads, is determined by a technician or clinician helping the patient. The socket 8 is for housing another element of the device 100, in particular a stimulator 1. The garment 10, such as textile or fabric garment, defines a hollow area 60 of substantially the same size and shape as the socket 8. The hollow area is designed to receive the socket 8. Thus, as shown for example in FIG. 1A, when the assembly 20 is put together with the garment 10, in such a way that the electrode 9 overlaps with the inner surface of the garment 10, the socket 8 shows up through the hollow area 60 of the garment 10, leaving the socket 8 ready to receive the stimulator 1.

The plurality of electrode pads 91 comprises at least one active electrode pad and at least one return electrode pad. The return electrode pad is normally larger than the active electrode pad. In a particular embodiment, there are up to 8 electrode pads defined as return electrode pads and up to 32 electrode pads defined as active electrode pads. For example, in a device for rehabilitating a foot, 16 active electrode pads and 4 return electrode pads may be used; and in a device for rehabilitating a hand, 32 active electrode pads and 8 return electrode pads may be used.

Figure 2A:
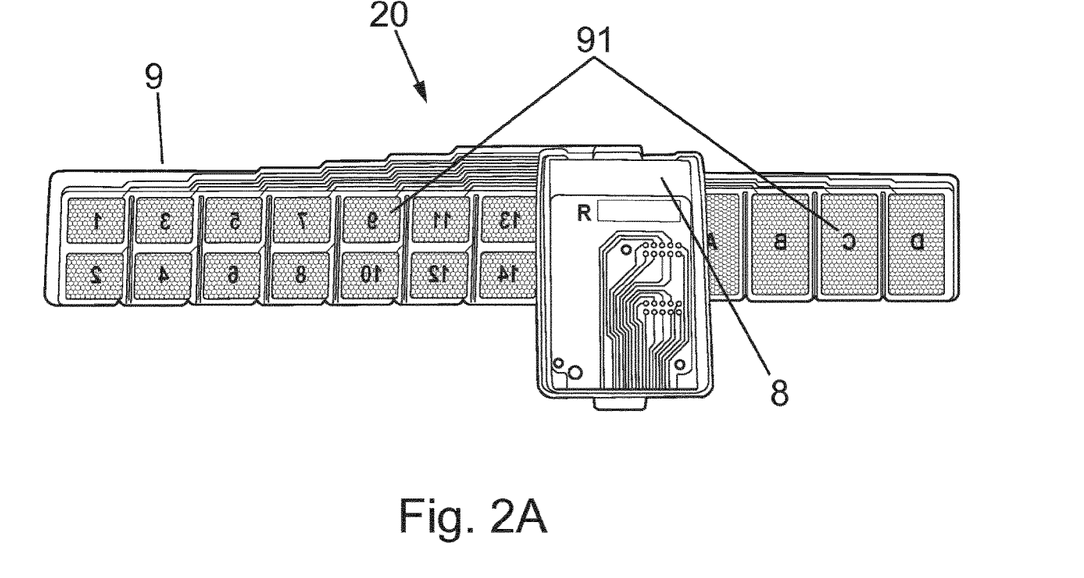
FIG. 2A shows an assembly comprising an electrode and a socket, wherein the electrode in turn comprises a plurality of electrode pads, according to a possible implementation of the disclosure.
Figure 2B:
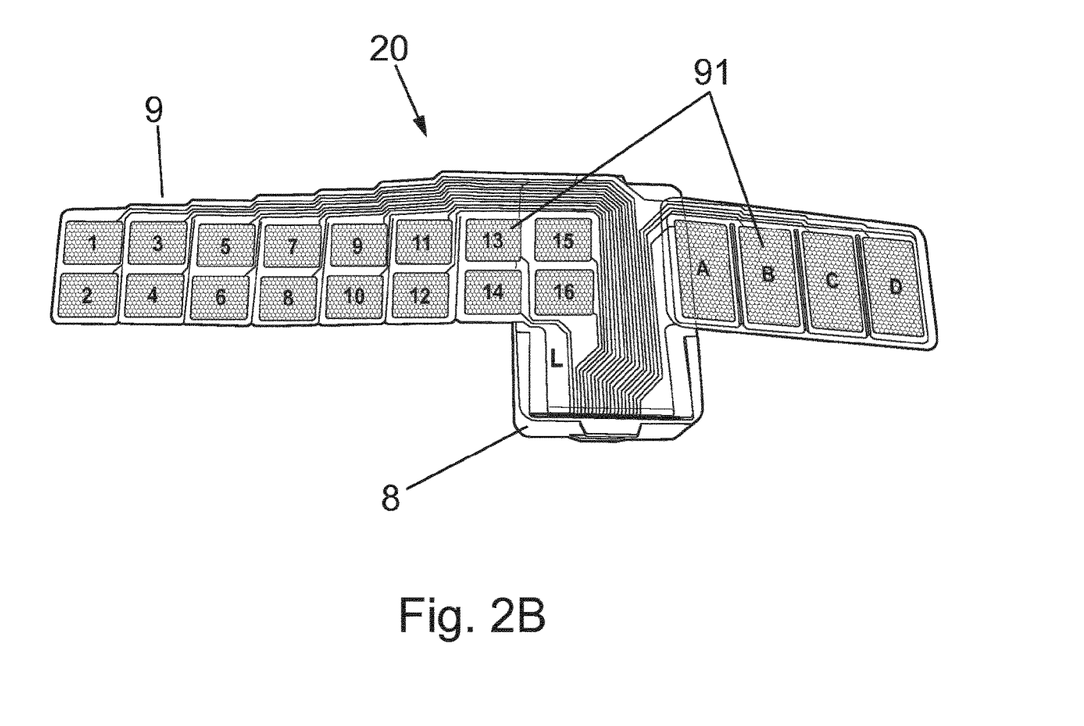
FIG. 2B shows a different view of the assembly of FIG. 2A.
Figure 2C:
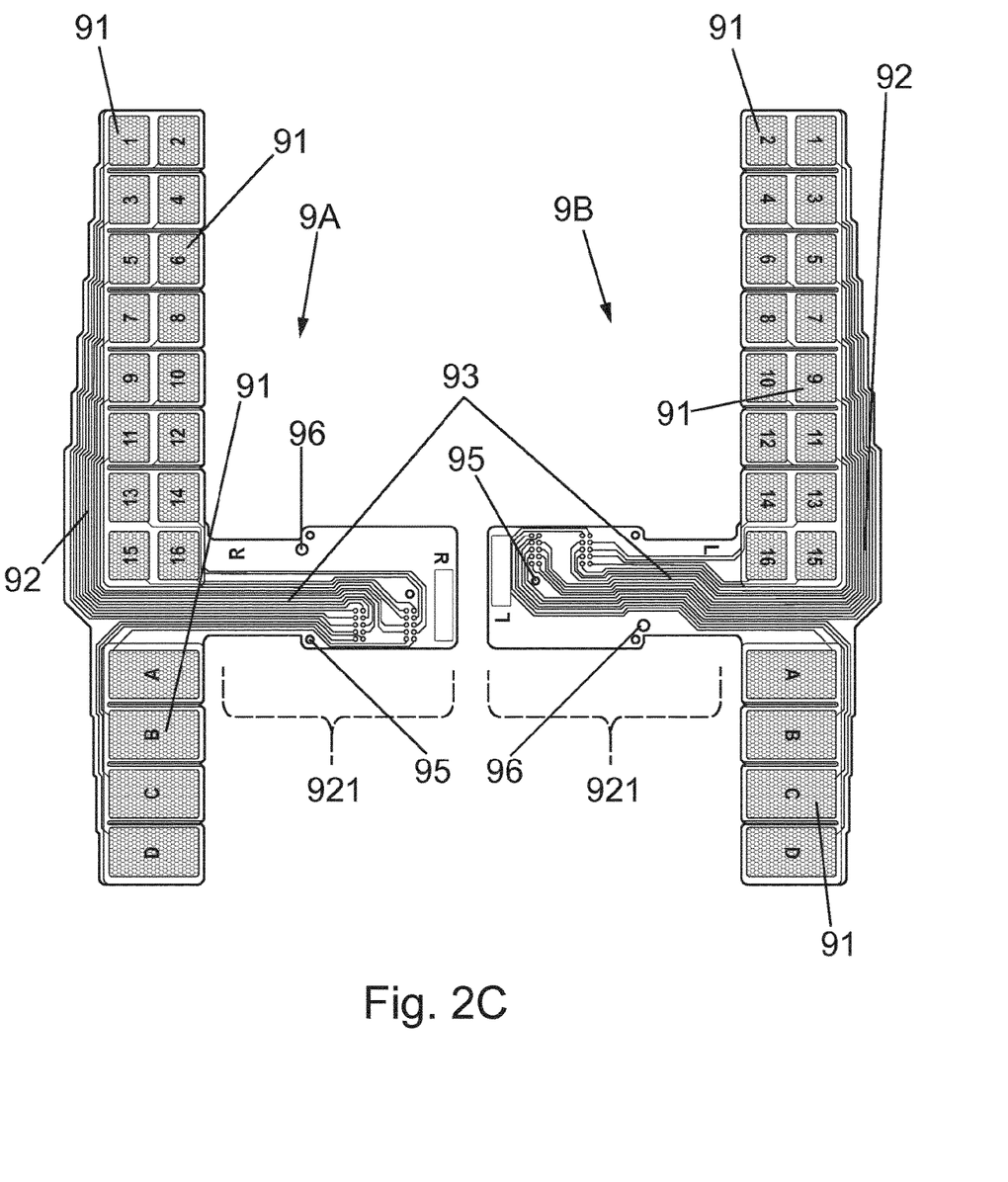
FIG. 2C shows two examples of electrodes or electrode patches, which may be comprised in an assembly according to the disclosure.

FIG. 2A shows an assembly 20 comprising a socket 8 and an elongated electrode 9 in turn comprising a plurality of electrode pads 91, according to a possible implementation of the disclosure, for example to be used in a device for rehabilitating a foot. FIG. 2B shows a different view—back view—of the assembly 20. The socket 8 is a rigid or semi-rigid housing, to which the electrode 9 is fixed (for example, glued). The socket 8 and the electrode 9 are firmly fixed to each other, forming a single part, thus providing the device 100 with a surface ready to guarantee that the pins protruding from the stimulator, not yet disclosed, will be in contact with the conductive paths, made for example of conductive ink, deposited on the substrate of the electrode 9. The socket 8 may be made of any rigid or semi-rigid material, such as plastic. The socket 8 has a slot through which the electrode 9 passes, in such a way that the portion of the electrode 9 not having electrode pads 91, can be bent after passing through the slot and adhered to the inner surface of the socket 8, that is to say, the surface of the socket configured to receive the stimulator 1. FIG. 2A shows the referred portion of the electrode 9 already bent and adhered to the socket 8. FIG. 2C shows two electrodes 9A, 9B designed to be fixed to respective sockets in order to integrate an assembly according to an embodiment of the disclosure. To the left, an electrode 9A to be used in a device 100 for stimulating a right leg is shown. To the right, an electrode 9B to be used in a device 100 for stimulating a left leg is shown. In both examples, the electrode has an insulating layer 92. The electrode pads 91 made or deposited on the substrate are covered with a hydrogel layer. The portion of the electrode 9A, 9B configured to be inserted through the slot made in the socket 8 and to be bent and adhered to the socket 8 is referred to with reference numbers 921. Conductive paths 93, such as silver or graphite paths, for example made with conductive ink, connecting the electrode pads 91 and different locations of portion 921, are also shown. In use of the device 100, when the stimulator 1 coupled to the socket 8, output pins 33 of the stimulator 1 are electrically connected to the conductive paths 93 of the electrode 9, 9A, 9B, and therefore electrically connected to respective electrode pads 91. Each portion 921 may also have a plurality of holes 95 designed to receive respective landmarks of the socket 8, as will be disclosed with reference to FIG. 7. The holes 95 may contribute to the correct positioning of portion 921 on the corresponding surface of socket 8. There may be another hole, for example a bigger one 96, that enables a protrusion in the socket to show up, as will be disclosed later.

The hydrogel layer covering the electrode pads 91 may be covered by a protective layer for protecting the hydrogel prior to the use of the electrode 9. The protective layer protects the hydrogel layer and prevents external dirt from damaging the hydrogel while it is not being used by a user. In embodiments of the disclosure, the electrode pads 91 allow controlled—spatial and temporal—current flow between active and return electrode pads. In a minimal configuration, the electrode 9 comprises at least two electrode pads 91 (one active electrode pad and one return electrode pad). FIGS. 2A and 2B show a possible design of electrode pads 91, to be used in a device for stimulating a leg, in which in a first portion of the electrode 9 there are two rows of electrode pads 91, each row having eight active electrode pads and four bigger return electrode pads. The first portion of electrode pads 91 is located at one side of the socket 8, while the second portion of electrode pads 91 is located at the opposite side of the socket 8. This configuration varies depending on the application of the system. For example, for stimulating hand function both the active and return electrode pads may be distributed on the whole substrate forming the electrode 9. In use of the device 100, the electrode pads 91 may be activated simultaneously (synchronous case) or sequentially (asynchronous case). In embodiments of the disclosure, the electrode pads 91 are rectangular with rounded edges to minimize so-called edge-effects (high current densities at the electrode edges). Other arbitrary shapes and number of electrode pads 91 could be utilized instead. The size and shape of the pads are chosen so as to produce comfortable but also selective stimulation. The assembly 20 formed by electrode 9 and socket 8 is reusable. After its use, it is recommended to separate the electrode 9 from the garment 10 and to cover the hydrogel layer with the protective film that had been removed in order dispose the electrode 9 to the skin.

Figure 5A:
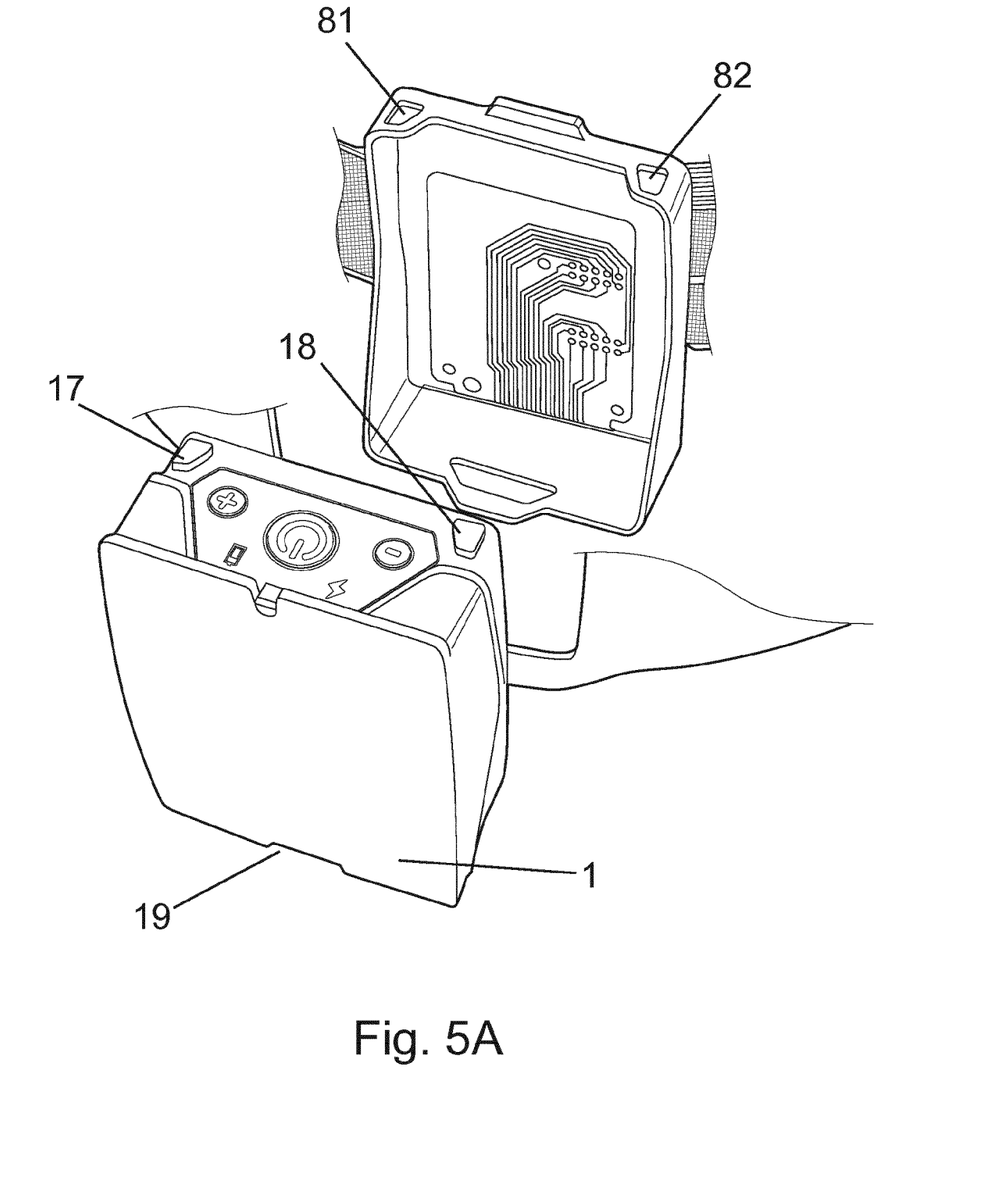
FIGS. 5A and 5B show side views of a stimulator comprised in a device for functional electrical stimulation according to a possible implementation of the disclosure.
Figure 5B:
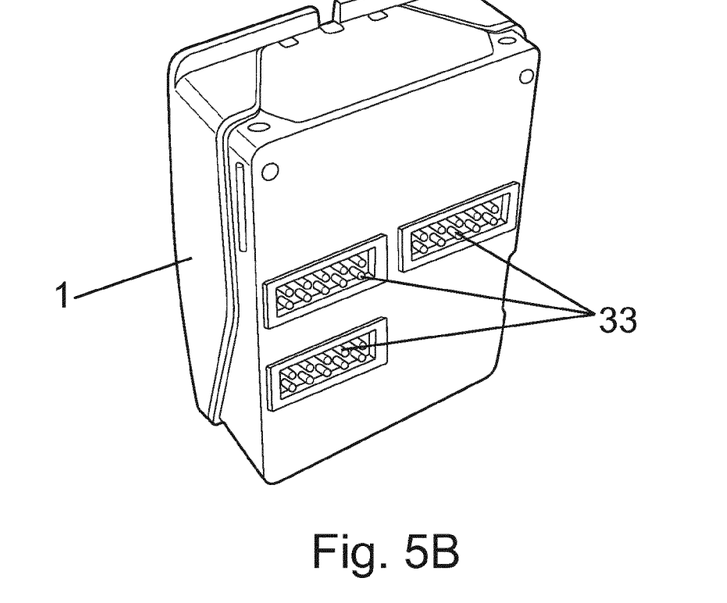

A third element of device 100 is stimulator 1. The stimulator 1 is a separate part of the device 100 and is designed to be housed in socket 8. A stimulator 1 according to a possible embodiment of the disclosure is shown in FIGS. 5A-5B. The stimulator 1 generates electrical pulses to be transferred to the user's skin through at least one electrode pad 91 from the plurality of electrode pads 91 of the electrode 9. The stimulator 1 comprises electronic means required to generate different stimulation patterns, such as pulse patterns, as ordered by a control application. The stimulator 1 performs control of parameters and delivery of stimulation based on control algorithms stored in memory means and executed in processing means. The stimulation control is real-time. In use of the device 100, the stimulator 1 generates electrical pulses that are transferred to the electrode 9 through corresponding output pins 33. In particular, in use of the device 100, the output pins 33 are electrically connected to the conductive paths 93 printed on the substrate of the electrode 9, 9A, 9B, and therefore electrically connected to respective electrode pads 91. The electronic means comprised in the stimulator 1 as well as the patterns of electrical pulses to be transferred to the user's skin, are out of the scope of the present disclosure.

In addition, the firmware or software embedded in the electronic means comprised in the stimulator 1, for example in processing means comprised in the stimulator 1, is not specific for the application, computer program or software used to control de device 100, for example from an external device, such as smart phone, tablet or the like. In other words, the stimulator 1 is a general-purpose stimulator, which makes the development of new control applications relatively easy. The stimulator 1 can elicit an electrical pulse with certain characteristics or parameters, such as frequency, pulse width, amplitude, compensation, time duration, etc. The firmware in the stimulator 1 has commands to establish the values of one or several of those parameters. As a consequence, the stimulator 1 is transparent to the specific use of the device 100, such as rehabilitation of foot, leg, hand, forearm, back..., since the use of the device 100 is determined by other elements of modules, such as the electrode 9, garment 10 and software application or computer program controlling the use of the device 100.

Figure 1B:
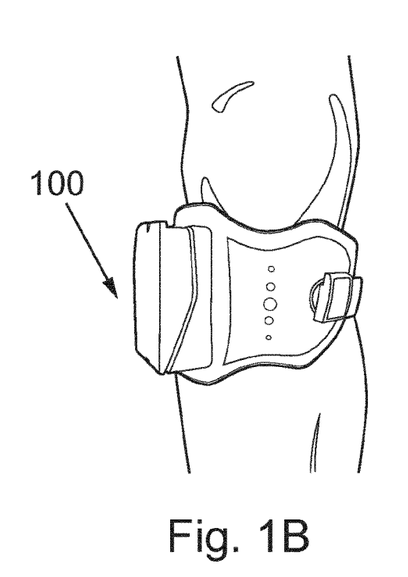
FIG. 1B shows a view of the device of FIG. 1A once assembled and mounted on a user's leg.
Figure 1C:
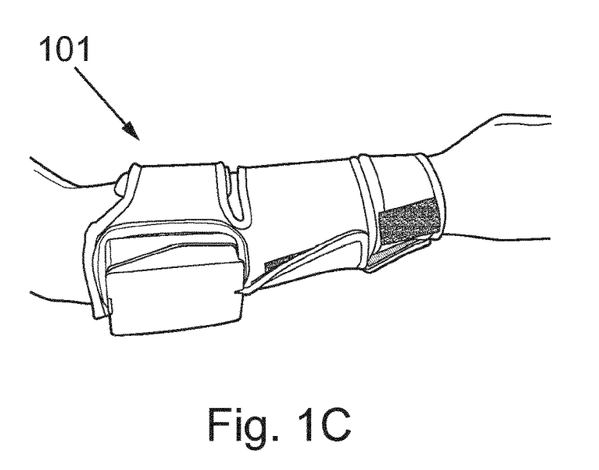
FIG. 1C shows a view of a device for functional electrical stimulation of a forearm, according to a possible implementation of the disclosure, once assembled and mounted on a user's arm.

FIG. 1B shows the device 100 of FIG. 1A once the different elements 10, 20, 1 have been assembled. In particular, the shown device 100 is mounted on a user's leg. The device 100 is assembled as follows: First, the assembly 20 comprising an electrode 9 and a socket 8 is assembled to or disposed on the garment 10. This is done by disposing a surface of the electrode 9 along an inner surface of the garment 10 while the socket 8 of the assembly 20 is received by the hollow area 60 defined by the garment 10. In other words, the socket 8 shows up through the hollow area 60 of the garment 10. When the hollow area 60 receives the socket 8, the electrode pads 91 comprised in electrode 9 are disposed in a fixed position with respect to the garment 10. The socket 8 then receives the stimulator 1, which is coupled or attached to the socket 8. In use of the device 100, the surface of the electrode 9 not in contact with the garment 10 is in contact with the user's skin, preferably by means of a hydrogel layer that acts as electrode pad-skin interface. Therefore, the electrode pads 91 comprised in the electrode 9 are in contact with the user's skin. The electronic means comprised in the stimulator 1 controls the activation/deactivation of stimulating electrical signals to be provided to the user's skin through the electrode pads 91. FIG. 1C shows a view of another device 101 for functional electrical stimulation, in this case of a user's hand, according to a possible implementation of the disclosure, once assembled and mounted on a user's arm.

Figure 3:
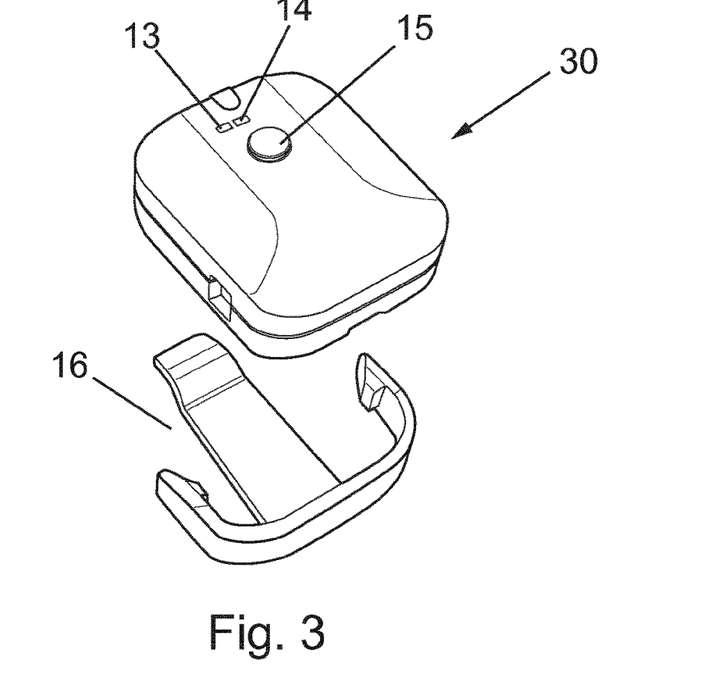
FIG. 3 shows a sensor and fixing means to attach the sensor, according to a possible implementation of the disclosure.

The device 100, 101 for functional electrical stimulation is part of a system for functional electrical stimulation. The system comprises, in addition to the device 100, 101, a sensor 30 for measuring the motion of the body member or limb and detecting different motion phases. FIG. 3 shows a sensor 30 and fixing means 16 to attach the sensor 30, according to a possible implementation of the disclosure. For example, if the device 100 is designed to be used in helping people suffering from foot drop, as is the case of the device shown in FIG. 1B, and therefore the device provides dorsal flexion and plantar flexion of the ankle, the sensor 30 measures the different movements of the corresponding foot and detects different gait phases. Thus, during gait, the device 100 electrically stimulates the motor nerves of the affected leg to achieve dorsal flexion and plantar flexion of the foot, so that the user improves his/her gait. In other words, the sensor 30 measures accelerations, angular velocities and orientation data and processes them and sends a stimulation command to the stimulator 1 as well as data, for example for determining the start and end of emission of electrical pulses through electrode pads 91, or to activate/deactivate stimulation patterns, thus stimulating the muscles in response to phases of body movement.

Non-limiting examples of sensors that may be used as sensor 30 are inertial sensors, such as inertial MEMS sensors or inertial measurement units (IMU), accelerometers, gyroscopes, magnetometers or any other suitable sensor. At least one sensor 30 is used. The at least one sensor 30 is configured to, in use of the system, measure data captured during movement (for example during walking or during arm or hand motion, as the case may be), process the captured data and transmit sensor signals indicative of the movement to the stimulator 1. The data captured by the sensor permits the sensor 30 to calculate the foot trajectory and gait phase when the user is walking, in an example in which the system is used to correct drop-foot, or the trajectory of other body parts, such as a hand or arm, in other examples. When the device is used to treat drop-foot, the sensor 30 is preferably located on the foot. Other designs of sensors different from the one shown in FIG. 3 may be used for other body parts, such as hands.

In embodiments of the disclosure, the sensor 30 is attached to the member or limb to be rehabilitated by means of fixing means 16, such as a clip, a collet or any other suitable attaching means. The sensor 30 may have an ON/OFF button or switch 15. It may also have a power indicator 13, that is to say, an indicator of available connection. The power indicator 13 may be a light indicator, such as a LED. The sensor 30 may also have a battery indicator 14, such as a light indicator, for example a LED. The sensor 30 is connected by means of a communication protocol to the stimulator 1. The connection between the sensor 30 and the stimulator 1 is preferably wireless, such as Bluetooth, Wi-Fi or RFID.

The sensor 30 has different functions: During calibration, it informs the stimulator 1 of how the given body member (foot, hand, etc.) is moving. During normal use of the system, it determines the onset and offset of the stimulation. It determines when to start and when to stop the stimulation. During normal use of the system, it records and evaluates user's movements and obtains important information about speed, symmetry, precision of trajectory, among others. In another operating mode, the sensor 30 may use the ON/OFF button 15 as external trigger button, to determine the onset/offset of the stimulation. This may be used, for example, in the event the movement is not sufficiently precise, in which case a therapist or clinician may push the ON/OFF button 15 in order to start or stop the stimulation.

Figure 4:
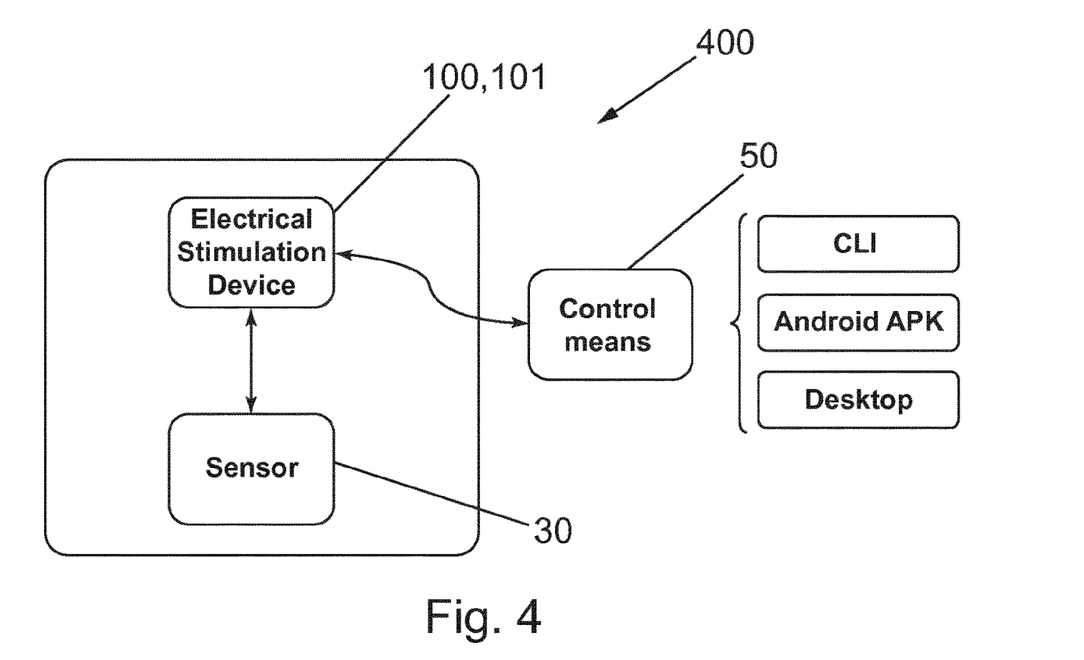
FIG. 4 shows in schematic form a system for functional electrical stimulation, including a device for functional electrical stimulation, a sensor and control means, according to a possible implementation of the disclosure.

The system comprises, in addition to the device 100, 101 and to the sensor 30, control means for controlling the operation of the device 100, 101. The control means may be embedded in any electronic device having processing means, such as a remote electronic device, for example a personal computer, a tablet, a smart phone or a Bluetooth adaptor, among others. The control means comprises a computer program, software or application for controlling and configuring the execution of the functional electrical stimulation device 100, 101. Having a non-proprietary communication makes the system capable of connecting to any electronic device. This permits the development of software applications in any conventional platform or operative system, such as Android, iOs, Windows, or any other, in a quick way, without modifying the firmware of the device 100, 101. In other words, in order to generate new programs, it is not necessary to develop new firmware, but solely a new application, or to add a new window with a new rehabilitation protocol to an existing application. FIG. 4 shows in schematic form the system 400, comprising a device 100, 101, a sensor 30 and control means 50 connectable to the device 100, 101 through a wireless interface. In particular, the control means 50 is connected to the stimulator 1. In other embodiments of the disclosure, the sensor 30 may have a direct communication with the control means 50 (not shown in FIG. 4). The control means 50 has control software that may be updated or replaced through different interfaces, such as command-line interface (CLI), different applications, such as Android applications, a desktop, or others.

Thus, the stimulator 1 comprised in device 100, 101 can communicate through a wireless protocol with an external device, such as smartphones, tablets or PCs comprising control means, such as a user application, from which the stimulation process can be controlled. Through a wireless connection, the user him/herself or a therapist can set specific stimulation parameters, initiate stimulation protocols (which are running on the stimulator) and observe stimulation execution. The stimulator 1 is responsible for the real-time control and delivery of the electrical pulses to the electrode pads 91 of the electrode 9, of stimulation based on control algorithms stored in memory means (for example in a memory comprised in the stimulator 1) and executed in processing means, for example upon user request. Through the stimulator 1, the device can be turned on and off, and some stimulation parameters, like the overall stimulation intensity, can be adjusted. The electrical pulses generated at the stimulator 1 are transferred to the electrode pads 91 through corresponding output pins 33. For example, each stimulation pattern comprises a set (at least one) of active electrode pads 91 among the electrode pads of the electrode 9, wherein each active electrode pad is given appropriate stimulation pulse amplitude, frequency, pulse width, etc. Each stimulation pattern also comprises specific time delays between successive electrode pad activations. The system of the present disclosure, based on the information captured by the sensor 30 positioned on a paretic body part (for example, leg or foot) of a patient, is able to modify the stimulation pattern during use of the system, that is to say, while the user is moving the body part to be rehabilitated.

Turning back to the stimulator 1, FIGS. 5A and 5B show respective side views of one according to embodiments of the disclosure. FIG. 5A is a side view of the front part of the stimulator 1, while FIG. 5B is a side view of the back part thereof. FIG. 5A also shows schematically a socket 8 configured to house the stimulator 1 in use of the device. The stimulator 1 is a compact box housing processing means for generating electrical pulses to be provided to the electrode pads 91 of the electrode 9. The values of the parameters that the stimulator 1 is capable of generating depend on the processing means and firmware embedded therein, and are out of the scope of the present disclosure. As a matter of example, the amplitude of the provided pulses may vary between 0-100 mA, the frequency of the provided pulses may vary between 0-100 Hz and the time duration of the provided pulses may vary between 0-700 μs. In addition, it is capable of controlling a large amount of electrode pads 91. For example, in a device for rehabilitating a foot, it may control up to 16 active electrode pads and 4 return electrode pads, while in a device for rehabilitating a hand, it may control up to 32 active electrode pads and 8 return electrode pads. It may provide a biphasic symmetric signal or a compensated biphasic signal. The stimulator 1 may have an ON/OFF button or switch 6. The stimulator 1 may also have a battery indicator 2, such as a light indicator, for example a LED. It may also have a power and connectivity indicator 3, that is to say, an indicator of available connection and power. This indicator 3 may be a light indicator, such as a LED. It may also have a stimulation indicator 4, such as a light indicator, for example a LED. It may also have a button for increasing intensity 5 and a button for decreasing intensity 7 of the stimulation being applied. When pressing this button, an acoustic signal may be emitted.

The stimulator 1 may have an input/output port or connector 31, such as a microUSB port, for different purposes, such as battery recharge and/or software updates. The stimulator 1 is connected by means of a communication protocol to the electronic device implementing the control means 50. The connection between the stimulator 1 and the electronic device (control means 50) is preferably wireless, such as Bluetooth, Wi-Fi or RFID.

Figure 6A:
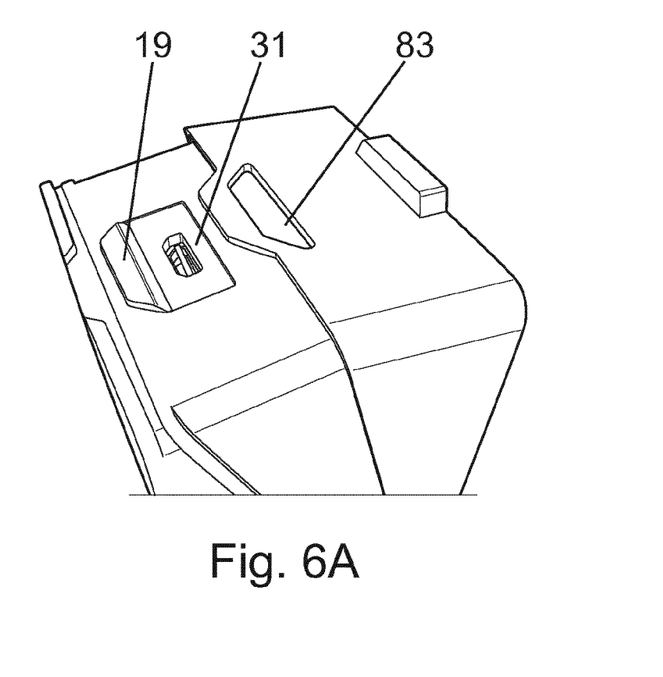
FIGS. 6A and 6B show a coupling between the socket and the stimulator according to a possible implementation of the disclosure.
Figure 6B:
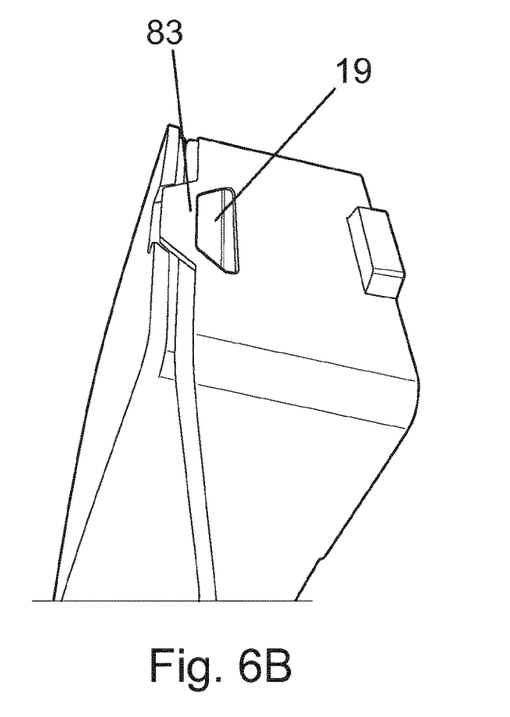
Figure 7:
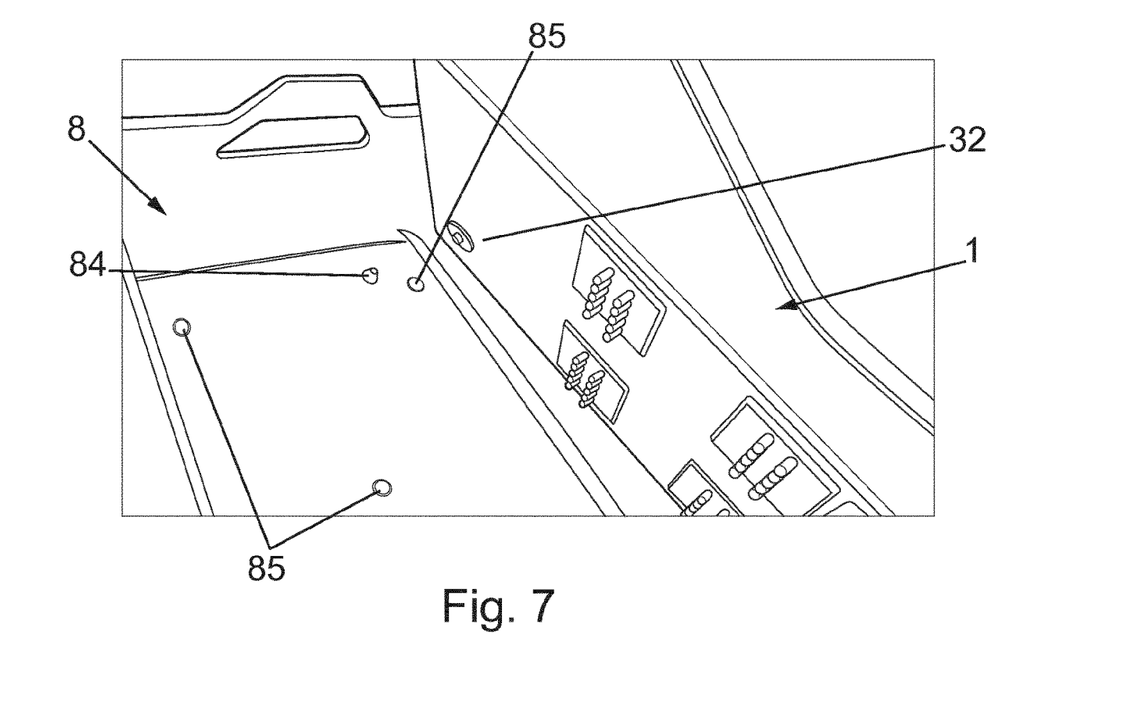
FIG. 7 shows a protrusion on the inner surface of the socket that matches a switch in the stimulator when the stimulator is housed in the socket, according to a possible implementation of the disclosure.

The mechanical coupling or attachment between the stimulator 1 and the socket 8 is secure and easy to implement. On the one hand, the socket 8 and the stimulator 1 have mechanical means for mechanically fixing the socket 8 and the stimulator 1 in a single position. In the shown embodiment, the stimulator 1 has two flanges 17, 18 (see for example FIG. 5A) configured to match corresponding recesses 81, 82 (see for example FIG. 1 or FIG. 5A) in socket 8. Besides, the socket 8 has a recess 83 configured to match a corresponding protrusion 19 in the stimulator 1 (see for example FIGS. 6A and 6B). This permits quick mounting of the stimulator in the socket in an easy way, for example with a single hand and without requiring the support of other people. On the other hand, the socket 8 is error-free (also referred to as poka yoke) owing to two reasons: As shown in FIGS. 6A-6B, when the stimulator 1 is coupled to the socket 8, the socket 8 covers the input/output port 31 of the stimulator 8, which implies that the battery of the stimulator 1 cannot be recharged during use of the device 100. In other words, the battery of the stimulator 1 can only be recharged when it is not coupled to the socket 8, that is to say, when the device 100 is not in use. In addition, as shown in FIG. 7, the stimulator 1 has a switch 32 that must be pressed in order for the stimulator 1 to be able to be switched on. If this switch 32 is not pressed, the stimulator 1 cannot be switched on. As shown in FIG. 7, the socket 8 has an additional protrusion 84 on its inner surface that matches the switch 32 in the stimulator 1 when the stimulator is housed in the socket, in such a way that the protrusion 84 presses the switch 32. In other words, the stimulator 1 can only be switched on when it is housed in a socket 8. Turning back to FIG. 2C, showing examples of electrodes 9A, 9B, hole 96 enables the protrusion 84 to show up from the electrode 9A, 9B, thus enabling the protrusion 84 to match the switch 32. As also shown in FIG. 7, the socket 8 has a plurality of landmarks 85 (for example, three landmarks 85 are illustrated) designed to match respective holes 95 made on portion 921 of the electrode 9A, 9B, in order to guarantee the correct positioning of the electrode 9A, 9B on the socket 8. In other words, each hole 95 in portion 921 is designed to receive respective landmarks 85 of the socket 8.

In use of the device 100, 101, when the stimulator 1 is housed in the socket 8, the electrical pulses are transferred from the stimulator 1 to the electrode pads 91 through corresponding output pins 33 disposed at the back surface of the stimulator 1, that is to say, at the surface of the stimulator 1 to be in contact with the socket 8 and therefore with the portion of the electrode 9, 9A, 9B to be bent and passed through the slot in the socket 8. FIG. 5B shows a particular embodiment, in which 3 groups of pins are shown. Other embodiments may be implemented depending on the design of the circuit or conductive paths disposed on the electrode 9, 9A, 9B. Also, depending on the application and type of electrode 9, 9A, 9B, some pins or groups of pins 33 may be disabled.

Figure 8A:
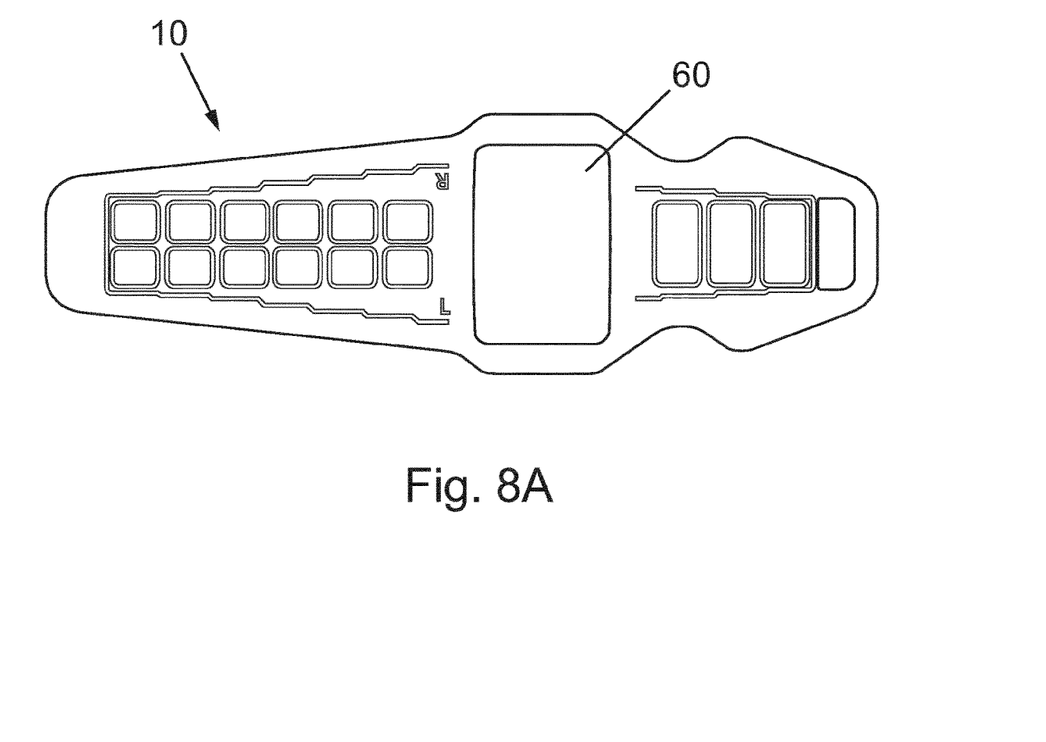
FIGS. 8A and 8B show respective inner and outer views of a garment for a device for functional electrical stimulation, according to a possible implementation of the disclosure. The garment shown in FIGS. 8A and 8B is intended to be placed on a user's leg.
Figure 8B:
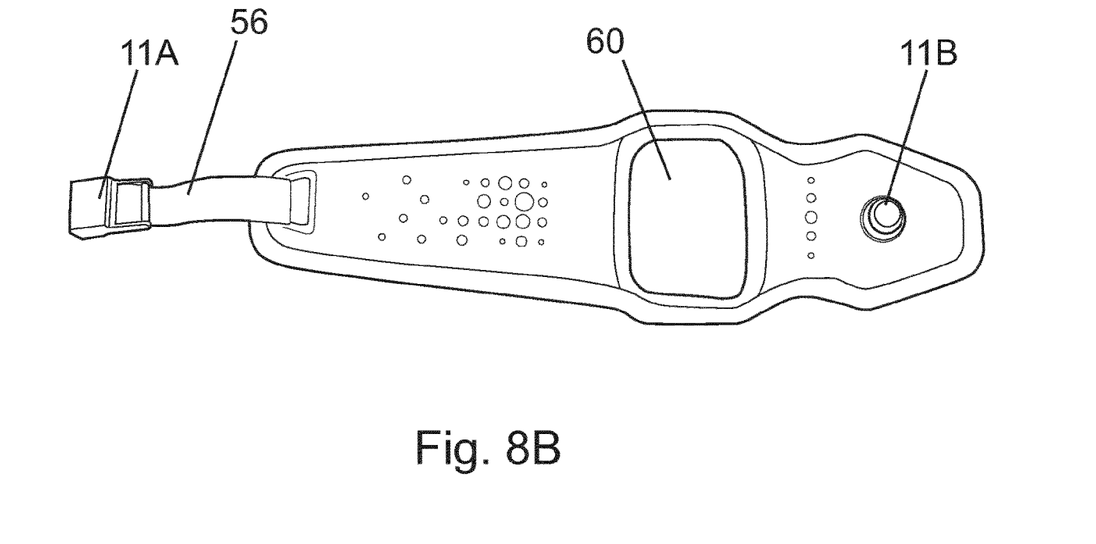

Turning back to the garment 10, such as textile or fabric garment, it ensures the correct adhesion or disposition of the electrode 9 to the user's skin. The garment 10 also ensures that the whole device 100, 101 remains united and compact. FIGS. 8A and 8B show two views of the garment 10 of an embodiment of the disclosure, designed to be worn on a user's leg. The garment 10 is provided with a locking system 11. In a particular example, the locking system 11 may be a magnetic-guided locking system. In the example shown in FIG. 8B, the locking system 11 is made up of two elements 11A, 11B configured to match: one of the elements 11A is disposed at one side of the hollow part of the garment 10 and the other element 11B is disposed at the opposite side of the hollow part. The two elements 11A, 11B are configured to match when the garment 10 is positioned on the limb or member to be rehabilitated. The locking system 11, which in this example is a magnetic-guided locking system 11, makes easier the closing and fixing of the garment 10. One element 11A may be disposed at the end of a belt 56, such as a clamping belt.

FIG. 8A shows a scheme of the inner surface of the garment 10, that is to say, the surface designed to be in contact with the electrode 9 when the device 100 is assembled. Like the socket 8, the garment 10 is error-free (also referred to as poka yoke), for different reasons: On its inner surface, the shape of the electrode 9 is screen-printed. This permits to place the electrode 9 exactly on the area of the garment 10 on which it must be placed. In addition, the inner surface of the garment 10 and the electrode 9, have a left-right indication (for example letter L and letter R), in order to make even more visible whether the electrode 9 has been correctly positioned or not. Besides, depending on the part of the body to be rehabilitated, the garment may be symmetric. For example, in a device for rehabilitating a foot (or generally, leg), as is the case of the device 100 of FIG. 1B, a single garment 10 may be used for the left leg and for the right leg. Screen-printed marks, such as circles in FIG. 8B, printed on the outer surface of garment 10, contribute to align it with respect to the user's body part on which it is placed. The combination of aligning means and fastening means 11, 11A, 11B, 56, enable the garment 10, as well as the assembled device 100, to be easily put on with the electrode pads 91 correctly located, even when handled by an impaired person.

Figure 8C:
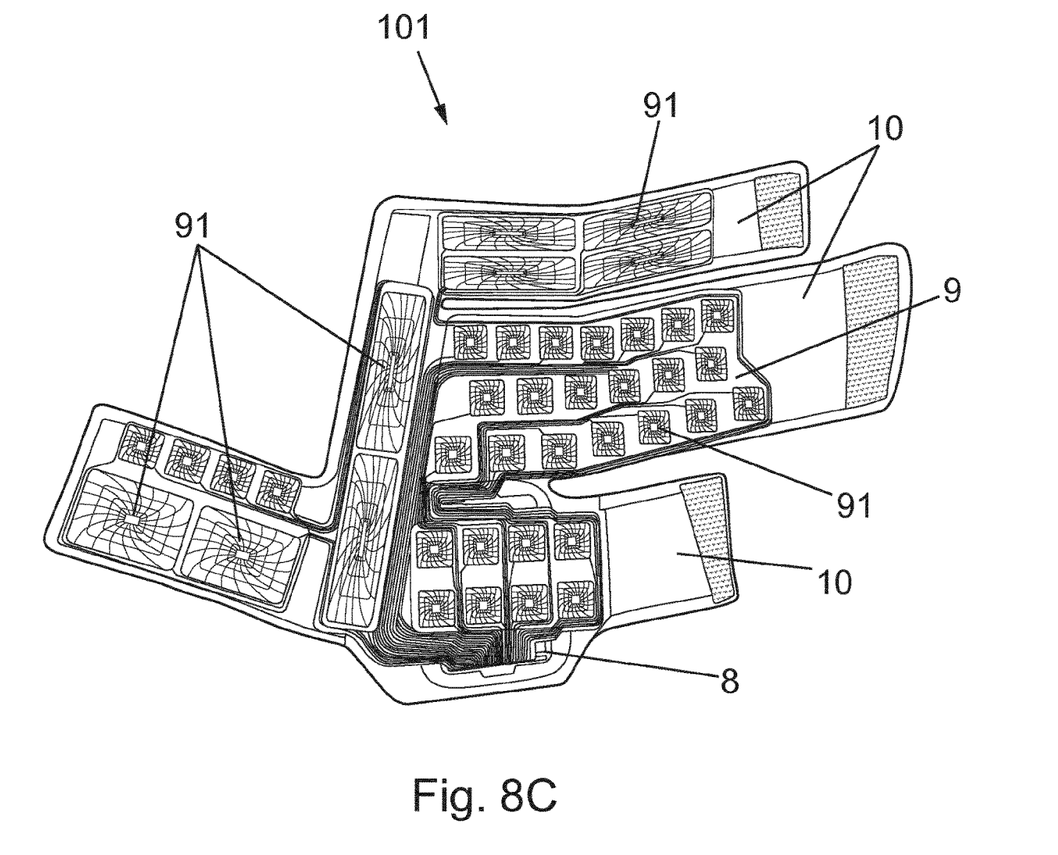
FIG. 8C shows a view of a garment having an assembly formed by an electrode and a socket, mounted therein, of a device for functional electrical stimulation of a forearm, as shown in FIG. 1C.
Figure 8D:
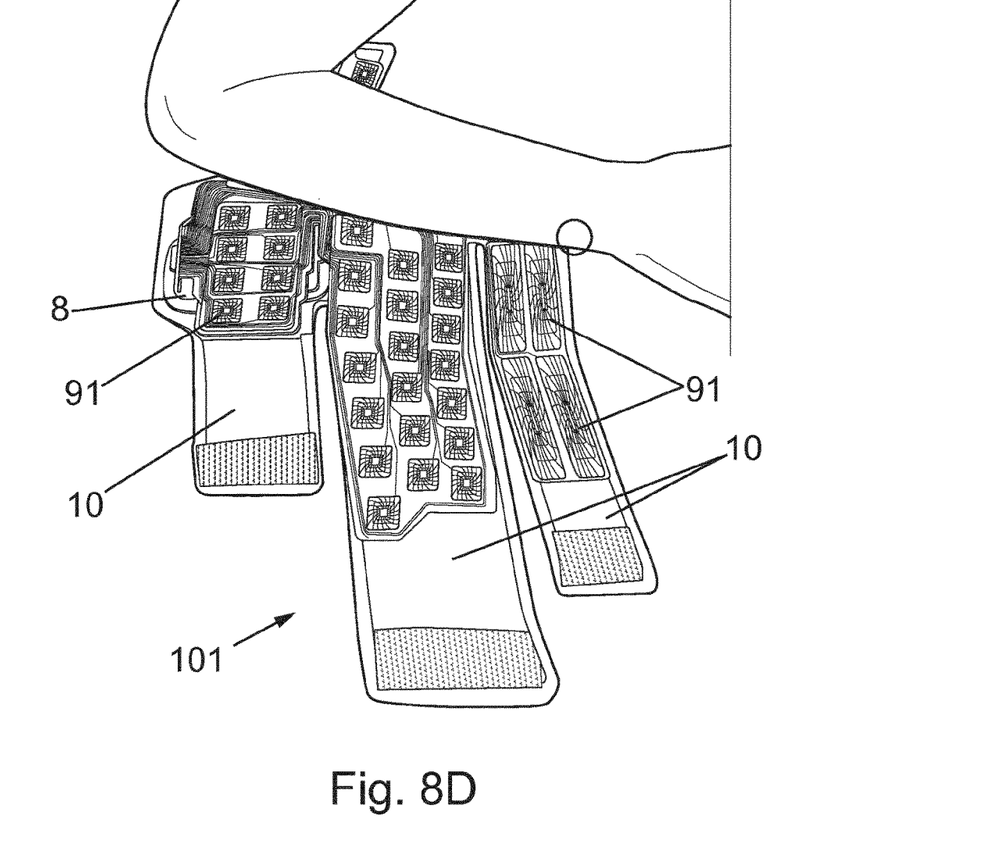
FIG. 8D shows the garment and assembly of FIG. 8C, in the position to be worn by a user.

FIGS. 8C and 8D show two views of another device 101 of an embodiment of the disclosure, designed to be worn on a user's arm. In particular, it is a device 101 designed to stimulate the muscles of the forearm. Like device 100, device 101 comprises a garment 10, an assembly comprising a socket 8 and an electrode or electrode patch 9, in turn comprising electrode pads 91, and a stimulator configured to be housed in the socket 8. The stimulator is not shown in the views of FIGS. 8C and 8D. The electrode or electrode patch 9 of this particular embodiment comprises 8 return electrode pads and 32 active electrode pads. The 8 return electrode pads are grouped in three different areas: two return electrode pads on the left (of FIG. 8C), two return electrode pads in the middle and four return electrode pads at the top. The 32 active electrode pads are also grouped in three different areas: four active electrode pads are in a row on the left of FIG. 8C, eight active electrode pads (2 rows of four pads per row) at the bottom and 20 active electrode pads in the middle of FIG. 8C (a first row of 7 pads, a second row of 6 pads and a third row of 7 pads). Regarding the garment 10 of this embodiment, it is made of three different portions. Each garment portion forms, in use of the device 101, a ring around the user's arm. Each of the three rings has a different diameter. The garment has an area which is common to the three portions, but each portion has a tongue or elongated part independent—separated—from the two other tongues or elongated portions. One of the tongues has a hollow area for receiving the socket. The three independent tongues, and therefore three independent rings around the user's arm in use of the device 101, enable the device 101 to adapt to the user's arm. The final appearance of the device 101, once worn by the user, is shown in FIG. 1C.

Figure 9:
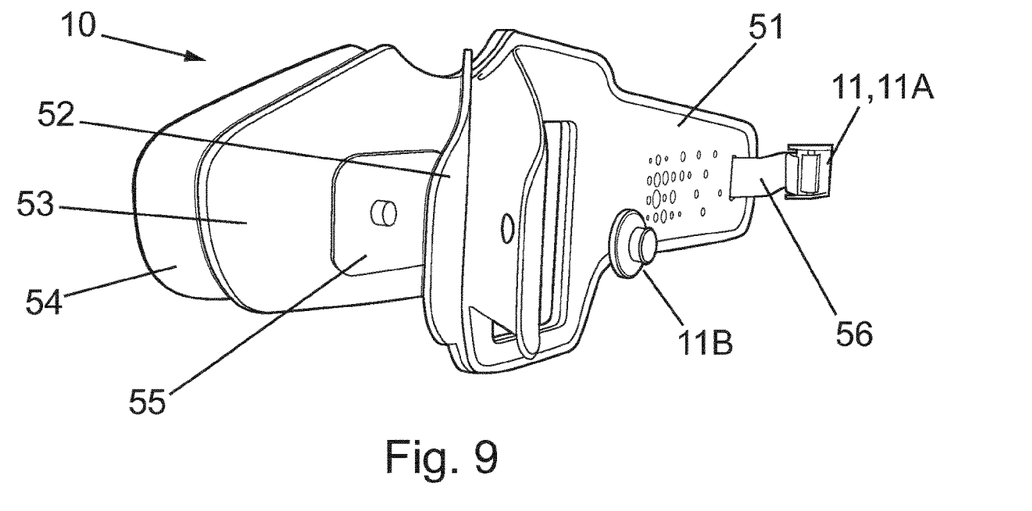
FIG. 9 shows an exploded view of a garment of a device for functional electrical stimulation, according to a possible implementation of the disclosure.

FIG. 9 shows an exploded view of a garment 10 according to a possible embodiment of the disclosure. The shown garment 10 has the following layers: an outer layer 51, which is screen-printed; a first intermediate layer 52 or outer intermediate layer, whose purpose is to improve the tactile feeling when the garment 10 is touched; a second intermediate layer 53 or inner intermediate layer, whose purpose is to improve comfort to the patient, for example by protecting the body member from the closing means, such as closing buckles 11; and an inner layer 54, which is screen-printed, and on which the electrode having electrode pads is disposed. The outer layer 51 and inner layer 54 may be made of a skin-friendly material. Non-limiting examples of such materials are soft Neoprene, Nylon, polyurethane, polyester, polyamide, polypropylene, silicone, cotton or any other material which is soft and flexible. All named materials could be used as woven, non-woven, single use fabric or laminated structures. In a particular example, the outer layer 51 and inner layer 54 are made of polyester, such as Coolmax®. The first intermediate layer 52 may be made, for example, of Polartec®. The second intermediate layer 53 may be made, for example, of felt. Between the first intermediate layer 52 and the second intermediate layer 53, preferably attached to the first intermediate layer 52, there is a structural part 55 which may support the assembly of socket and stimulator, the locking means 11, 11A, 11B and the clamping belt 56 in embodiments comprising locking means and/or a clamping belt. The structural part 55 may be made, for example, of polycarbonate. The outer screen-printing (of the outer layer 51) also contributes to the correct positioning of the garment 10.

Next, different stages of mounting on a user's leg a device 100 for functional electrical stimulation, for correction of drop-foot, are disclosed. First, the set formed by the garment 10 and the assembly 20 comprising electrode 9 and socket 1, is disposed on the leg. In particular, it is placed under the user's knee. The circles screen-printed on the garment 10 contribute to align the set with respect to the user's knee. The garment 10 may then be locked by means of fixing means. In addition to the fixing means, the garment 10 may be adjusted by manipulating a clamping belt. Next, the stimulator 1 is housed in the socket 8. The final appearance of the device 100, once worn by the user, is shown in FIG. 1B. In order to use the complete system for functional electrical stimulation, a sensor 30 is disposed on the user's feet of the leg under rehabilitation. The sensor 30 may be for example clipped to the user's shoe. Now, with control means 50 implemented, for example, in a mobile telephone, tablet or similar, an application for controlling the execution of the device for functional electrical stimulation is run. In use of the system, while the user is walking, the stimulator 1 receives signals provided by the sensor 30 for modifying the stimulation patterns during walking.

In this text, the term "comprises" and its derivations (such as "comprising", etc.) should not be understood in an excluding sense, that is, these terms should not be interpreted as excluding the possibility that what is described and defined may include further elements, steps, etc.

The disclosure is obviously not limited to the specific embodiment(s) described herein, but also encompasses any variations that may be considered by any person skilled in the art (for example, as regards the choice of materials, dimensions, components, configuration, etc.), within the general scope of the disclosure as defined in the claims.

The invention claimed is:

1. A device for functional electrical stimulation, comprising:
   a garment mountable on a user's body part,
   an assembly comprising a socket and an electrode in turn comprising a plurality of electrode pads, the electrode being fixed to the socket, the electrode and the socket forming a single part, and
   a stimulator comprising control means configured for controlling the activation/deactivation of stimulating electrical signals to be provided to at least some of said plurality of electrode pads and an input/output port, wherein the garment defines a hollow area configured to receive the socket, the socket being configured to receive the stimulator, wherein in use of the device, when the socket is received by said hollow area and the stimulator is housed in the socket, a first portion of the electrode is in contact with an inner surface of the garment, said plurality of electrode pads of the electrode being in a fixed position with respect to the garment, and a second portion of the electrode is in direct contact with a surface of the socket for receiving the stimulating electrical signals delivered by the stimulator, and wherein the socket has means configured for guaranteeing that when the stimulator is coupled to the socket, the socket covers the input/output port of the stimulator.

2. The device according to claim 1, wherein the garment has fastening means configured to secure the garment to or around the user's body part.

3. The device according to claim 1, wherein the electrode comprises a substrate on which said plurality of electrode pads are implemented.

4. The device according to claim 1, wherein the electrode comprises a conductive layer disposed on the surface of said plurality of electrode pads intended to be in contact with the user's skin.

5. The device according to claim 1, wherein the assembly comprising the electrode and the socket is reusable.

6. The device according to claim 1, wherein the control means comprised in the stimulator configured for controlling the activation/deactivation of stimulating electrical signals to be provided to at least some of said plurality of electrode pads, are electronic means configured for generating electronic patterns.

7. The device according to claim 1, wherein the socket has means configured for guaranteeing that the stimulator cannot be switched on when it is not received in the socket.

8. The device according to claim 1, wherein the outer surface of the garment has a plurality of screen-printed marks configured for aligning the device with respect to the user's body part on which it is placed.

9. The device according to claim 1, wherein the surface of the garment is configured to have the electrode disposed thereon, said surface having a shape of said plurality of electrode pads screen-printed.

10. The device according to claim 1, wherein the garment has a left-right indication configured to make more visible whether the electrode has been correctly positioned or not.

11. The device according to claim 1, wherein the garment is made of a plurality of portions, wherein each portion of said plurality of portions, in use of the device, forms a ring around the user's arm; wherein the garment has an area which is common to the plurality of portions and each portion of said plurality of portions has a tongue or elongated part independent from the tongues or elongated parts of the other portions of said plurality of portions.

12. A system comprising:
 a device configured for functional electrical stimulation according to claim 1, and
 a sensor configured to be positioned on either said body part of the user or in the proximity thereto, the sensor being configured to, in use of the system, measure information during movement and emit sensor signals indicative thereof, to be received and processed by the stimulator comprised in the device,
 the stimulator controlling the activation/deactivation of stimulating electrical signals to be provided to at least some of said plurality of electrode pads as a function of the sensor signals provided by the sensor.

13. The system according to claim 12, wherein the stimulator and the sensor are connected through a wireless connection.

14. The system according to claim 12, further comprising control means configured for controlling the operation of the device, the control means being embedded in an electronic device having processing means, the control means comprising a computer program, software or application for controlling and configuring the execution of the device, the control means communicating with the stimulator comprised in the device through a wireless protocol.

* * * * *